(12) United States Patent
Hassler, Jr.

(10) Patent No.: US 10,070,918 B2
(45) Date of Patent: Sep. 11, 2018

(54) ABLATOR FOR SPINAL DISC REMOVAL

(71) Applicant: Stryker European Holdings I, LLC, Kalamazoo, MI (US)

(72) Inventor: William Hassler, Jr., Portage, MI (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 789 days.

(21) Appl. No.: 14/603,846

(22) Filed: Jan. 23, 2015

(65) Prior Publication Data

US 2015/0201999 A1 Jul. 23, 2015

Related U.S. Application Data

(60) Provisional application No. 61/930,636, filed on Jan. 23, 2014.

(51) Int. Cl.
*A61B 18/14* (2006.01)
*A61B 18/12* (2006.01)
*A61M 1/00* (2006.01)
*A61M 3/02* (2006.01)
*A61F 2/44* (2006.01)
(Continued)

(52) U.S. Cl.
CPC ...... *A61B 18/1492* (2013.01); *A61B 18/1233* (2013.01); *A61B 18/1482* (2013.01); *A61M 1/0058* (2013.01); *A61M 3/0283* (2013.01); *A61B 1/00135* (2013.01); *A61B 1/3135* (2013.01); *A61B 2018/00339* (2013.01); *A61B 2018/00577* (2013.01); *A61B 2018/00595* (2013.01); *A61B 2018/00625* (2013.01); *A61B 2018/00666* (2013.01); *A61B 2018/00708* (2013.01); *A61B 2018/00875* (2013.01); *A61B 2018/00982* (2013.01); *A61F 2/442* (2013.01)

(58) Field of Classification Search
CPC ............... A61B 18/14; A61B 18/1492; A61B 2018/00577; A61B 2018/00636; A61B 2018/00666–2018/00678; A61B 2018/00875; A61B 2018/00339; A61F 2/4611; A61M 3/0283
See application file for complete search history.

(56) References Cited

U.S. PATENT DOCUMENTS

5,437,665 A * 8/1995 Munro ................... A61B 18/14
606/41
5,540,684 A 7/1996 Hassler, Jr.
(Continued)

*Primary Examiner* — Eric S Gibson
(74) *Attorney, Agent, or Firm* — Lerner, David, Littenberg, Krumholz & Mentlik, LLP (57) ABSTRACT

An ablator system includes a tool for insertion into a patient to ablate tissue. A system also includes a control unit and a pump system. A tool is adapted to receive RF energy from a control unit and ablate tissue between an electrode embedded in the tool and a return element. A control unit measures impedance between the electrode and return element and can disable the RF energy supply if the impedance is outside of an acceptable threshold value range. A tool has at least one port through which irrigation and suction are supplied by the pump system to remove debris. A tool houses a scope in an internal channel to provide visual feedback of the surgical site. A system therefore provides a tool that is visually guided to a surgical site, ablates tissue while utilizing active safety measures, and provides irrigation and suction to clear debris from the surgical site.

20 Claims, 7 Drawing Sheets

(51) Int. Cl.
*A61B 18/00* (2006.01)
*A61B 1/00* (2006.01)
*A61B 1/313* (2006.01)

(56) References Cited

U.S. PATENT DOCUMENTS

| | | | |
|---|---|---|---|
| 5,595,565 A | 1/1997 | Treat et al. | |
| 5,980,504 A | 11/1999 | Sharkey et al. | |
| 6,095,149 A | 8/2000 | Sharkey et al. | |
| 6,264,651 B1 * | 7/2001 | Underwood | A61B 18/12 604/114 |
| 6,464,695 B2 * | 10/2002 | Hovda | A61B 18/148 128/898 |
| 6,468,274 B1 * | 10/2002 | Alleyne | A61B 18/1206 604/114 |
| 6,712,811 B2 * | 3/2004 | Underwood | A61B 18/1206 128/898 |
| 6,726,684 B1 * | 4/2004 | Woloszko | A61B 18/148 606/32 |
| 6,832,997 B2 * | 12/2004 | Uchida | A61B 18/148 606/41 |
| 7,104,986 B2 * | 9/2006 | Hovda | A61B 18/12 128/898 |
| 7,144,397 B2 * | 12/2006 | Lambrecht | A61B 5/1076 606/79 |
| 7,270,658 B2 | 9/2007 | Woloszko et al. | |
| 7,357,798 B2 * | 4/2008 | Sharps | A61B 18/12 606/32 |
| 7,572,251 B1 * | 8/2009 | Davison | A61B 18/12 604/500 |
| 7,771,419 B2 | 8/2010 | Carmel et al. | |
| 7,883,458 B2 | 2/2011 | Hamel | |
| 9,668,803 B2 * | 6/2017 | Bhushan | A61B 18/1233 |
| 9,717,552 B2 * | 8/2017 | Cosman | A61B 18/1482 |
| 2003/0130738 A1 * | 7/2003 | Hovda | A61B 18/148 623/17.11 |
| 2007/0083193 A1 * | 4/2007 | Werneth | A61B 5/0422 606/41 |
| 2007/0185519 A1 | 8/2007 | Hassler et al. | |
| 2008/0167645 A1 * | 7/2008 | Woloszko | A61B 18/1206 606/40 |
| 2008/0208187 A1 * | 8/2008 | Bhushan | A61B 18/1206 606/41 |
| 2008/0255642 A1 * | 10/2008 | Zarins | A61B 18/1206 607/99 |
| 2009/0076492 A1 * | 3/2009 | Behnke | A61B 18/18 606/33 |
| 2010/0286477 A1 | 11/2010 | Ouyang et al. | |
| 2014/0276697 A1 * | 9/2014 | Greenberg | A61B 18/22 606/15 |
| 2015/0201999 A1 * | 7/2015 | Hassler, Jr. | A61B 18/1492 623/17.16 |
| 2015/0320481 A1 * | 11/2015 | Cosman, Jr. | A61B 18/1482 606/35 |
| 2016/0278841 A1 * | 9/2016 | Panescu | A61B 18/1206 |
| 2017/0189105 A1 * | 7/2017 | Panescu | A61B 5/0422 |

\* cited by examiner

ABLATOR FOR SPINAL DISC REMOVAL

CROSS-REFERENCE TO RELATED APPLICATIONS

The present application claims the benefit of U.S. Provisional Patent Application No. 61/930,636, filed on Jan. 23, 2014, the disclosure of which is hereby incorporated herein by reference.

BACKGROUND OF THE INVENTION

The present invention is directed to an improved method of removing spinal disc material, more particularly, to an ablation procedure for accomplishing same.

The vertebrae that form the spine are separated by small discs. It is often necessary for such discs to be removed, either partially or completely, as part of a surgical procedure. For instance, a herniated disc may allow tissue contained within it to compress a nerve root along the spine. This pressure can cause significant discomfort or pain to the affected person. One procedure to alleviate this pressure is spinal decompression. This procedure involves accessing the particular spinal area and removing all or a portion of the spinal disc. Typically, this has been accomplished through the use of cutting instruments operated through cannulae or retractors. However, other methods have been utilized, including radio frequency (RF) energy to remove the spinal disc tissue.

However, these prior attempts to remedy herniated discs each have their own drawbacks. For instance, the use of cannulae or retractors limits the amount of the disc space that is viewable by the surgeon and often requires the use of specialized tools that may be difficult to utilize efficiently. Likewise, prior RF methods for disc ablation have been relatively rudimentary.

Therefore a need exists for an improved tool and method for removing spinal disc material, for instance, to decompress a herniated disc.

BRIEF SUMMARY OF THE INVENTION

An RF surgical system according to one aspect of the disclosure includes an ablator tool with a proximal end and a distal end. At least one port may extend from the proximal end to the distal end. An ablator tool preferably includes a first electrode with an electrode tip extending beyond the distal end of the tool to expel energy and a return element for collecting expelled energy. A return element can be a second electrode or an electrocautery pad. An ablator tool can also have at least one channel formed within it extending from the proximal end toward the distal end and preferably terminates prior to reaching the distal end. A scope to provide visualization can be housed inside the channel. An ablator tool can be created by modifying a multiple port scope having at least one electrode in some embodiments.

A surgical system according to one embodiment of the first aspect includes a control unit connected to a first electrode and a return element. The control unit desirably provides RF energy to a first electrode and measures impedance between a first electrode and return element. Preferably, the control unit discontinues power to a first electrode if the measured impedance is outside an acceptable range of impedance values.

The RF surgical system desirably includes a pump system to provide irrigation and suction at a surgical site, preferably through one or more ports in an ablator tool. In some embodiments, the irrigation may pour through an irrigation flow through hole in an electrode tip extending from the distal end of an ablator tool to wash away any debris from the tool.

In some embodiments, the ablator tool is flexible, and can be manipulated through the use of a self-articulating scope or may have an articulation driver incorporated into ablator tool itself.

Another aspect of the present invention is a method of ablating tissue. The method includes maneuvering an ablator tool into a spinal disc based on visual feedback provided by an ablator tool, transferring energy from a first electrode, through tissue, and into a return element, and providing irrigation and suction to a surgical site through an ablator tool. The tissue can be ablated during the energy transfer from the first electrode through the tissue and into a second electrode. In other embodiments, energy can be transferred from a first electrode, into tissue, and into an electrocautery pad. The method preferably also includes a control unit measuring impedance between a first electrode and a return element. A control unit may be utilized to compare the measured impedance to a threshold value and temporarily cease to provide energy if the measured value is outside an acceptable range of impedance values.

A threshold value range may be determined by sampling different tissues at a surgical site to measure their impedance and a range may be based on those values. The method of ablating tissue can utilize a flexible ablator tool in some embodiments. The method desirably uses a self-articulating device for manipulating the flexible ablator tool, most preferably a self-articulating scope or an ablator tool having an articulation driver embedded in it.

The method according to one aspect of the invention may include determining if more discs should be ablated after ablation of a disc has occurred. When more than one disc should be ablated, the method can include repeating the process until all necessary discs have been ablated. The method may also include removing the ablator tool from the patient once all necessary discs have been ablated. The method according to one aspect of the disclosure desirably includes ablating bulging tissue from a herniated disc.

Another aspect of the disclosure is a method of spinal surgery which preferably includes maneuvering an ablator tool into a spinal area, assisted by visual feedback. The method can also include vaporizing at least part of a spinal disc, transporting debris from the site via irrigation provided by the ablator tool, removing the ablator tool from the void created during the vaporization process, and implanting an interbody device in the unoccupied void. The method according to one embodiment provides access to a disc space from a lateral, posterior, or anterior direction. The size of a disc space created can vary to accommodate different interbody devices.

BRIEF DESCRIPTION OF THE DRAWINGS

A more complete appreciation of the subject matter of the present invention and the various advantages thereof can be realized by reference to the following detailed description, in which reference is made to the accompanying drawings.

DETAILED DESCRIPTION

Although the invention disclosed in this application has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended exemplary claims.

In a first embodiment, illustrated in FIGS. 1-4, a spinal disc ablator system 100 includes ablator tool 101 electrically connected to a control unit 102 and fluidly connected to a pump system 105. Ablator system 100 also includes a scope 106 that can be inserted into an ablator tool 101. As will be discussed more fully below, ablator system 100 is designed such that tool 101 can be inserted into a patient's body, visually guided into a spinal disc, used to ablate intended tissue while minimizing or eliminating damage to surrounding tissue, and used to irrigate a surgical site and remove any debris.

Figure 2:
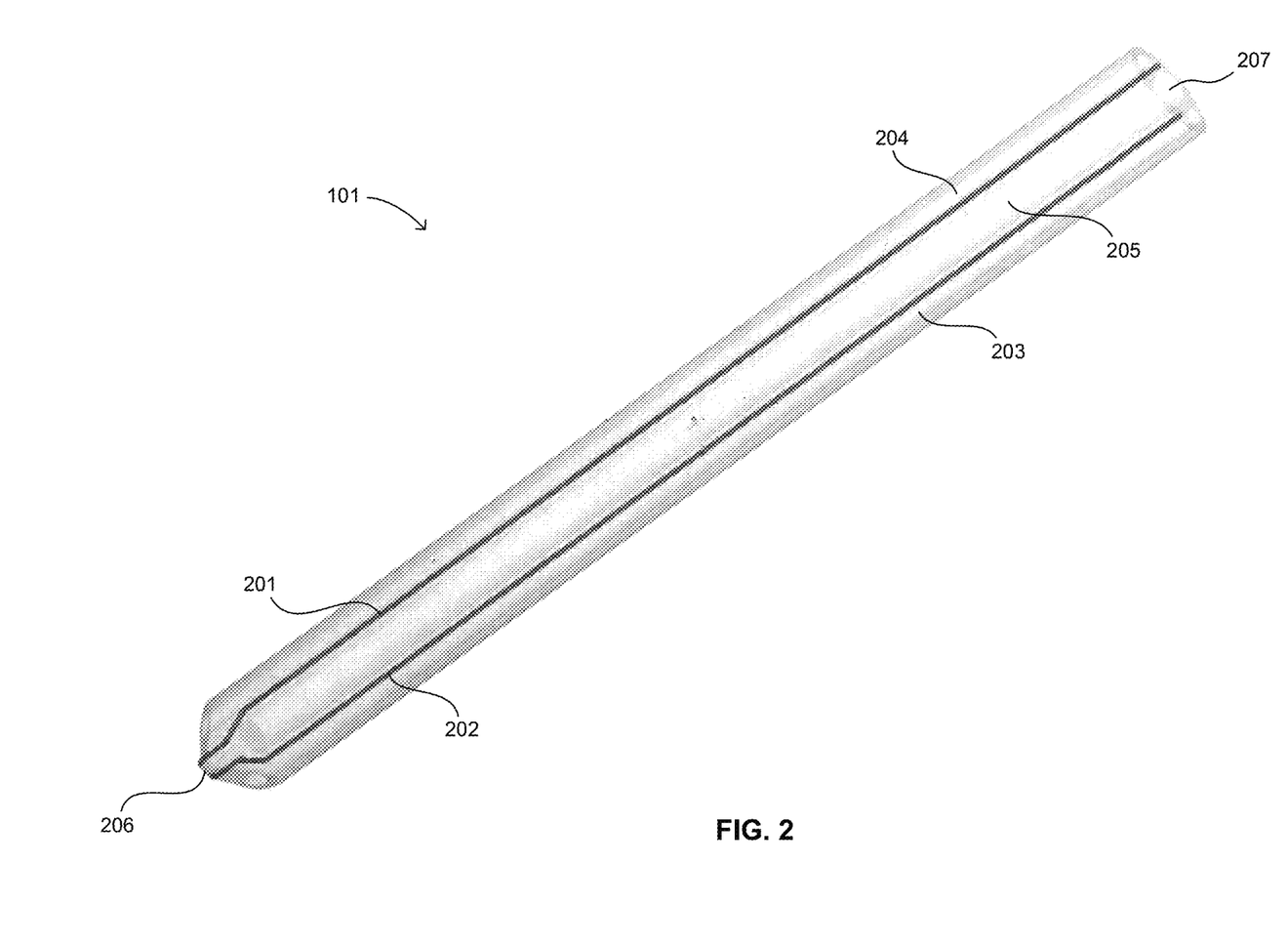
FIG. 2 is a perspective view of the ablator tool of the system shown in FIG. 1.

Ablator tool 101 is an elongated member with a proximal end and a distal end. With reference to FIG. 2, ablator tool 101 has an ovular shape with a rounded, conical shaped distal end 206 to facilitate insertion into the body of a patient while minimizing the risk of internal injuries. In other embodiments where alternative internal features of an ablator tool may be included, the cross-section may have a different shape, for example, circular.

Ablator tool 101, as shown in FIGS. 1-4 has a substantially rigid structure. In other embodiments, an ablator tool could be flexible to increase maneuverability during insertion. Flexion can be achieved by incorporating an outer wall with some portions thinner than others, thereby allowing an ablator tool to bend at those thin portions. A fan-fold design could also be used and may have an additional benefit of preventing overextension once the tool has reached its maximum designed curvature. As a maximum bend is approached the sections of the fan-fold can come into contact with each other to prevent further flexing in that direction.

Ablator tool, as shown in FIGS. 1-4, is depicted as an instrument manufactured according to this specification. However, ablator tool could also be created by modifying a multiport scope (such as the Olympus TriPort15) to include the additional features of ablator tool into the scope.

Ablation occurs when RF energy from a control unit flows through the tissue between an electrode and a return element. The tissue exhibits resistance to the current flow which is converted to thermal energy. When enough energy is supplied, the tissue can be heated to its vaporization point.

As shown, a first electrode 201 and a return element, in the form of a second electrode 202, are embedded directly in the ablator tool 101. The body of an ablator tool 101 is therefore preferably made from an electrically insular material (for example, polycarbonate, acrylic, rubber) to prevent RF energy arcing from one electrode to the other inside the tool. In fact, the electrodes 201, 202 are on diametrically opposed sides of the channel 205 to further increase the electrical insulation inside the tool 101 (see FIG. 4). Positioning the electrodes on opposing sides of the channel also increases the area between the electrodes through which the scope gathers visual images of the tissue between the electrode tips.

Figure 3:
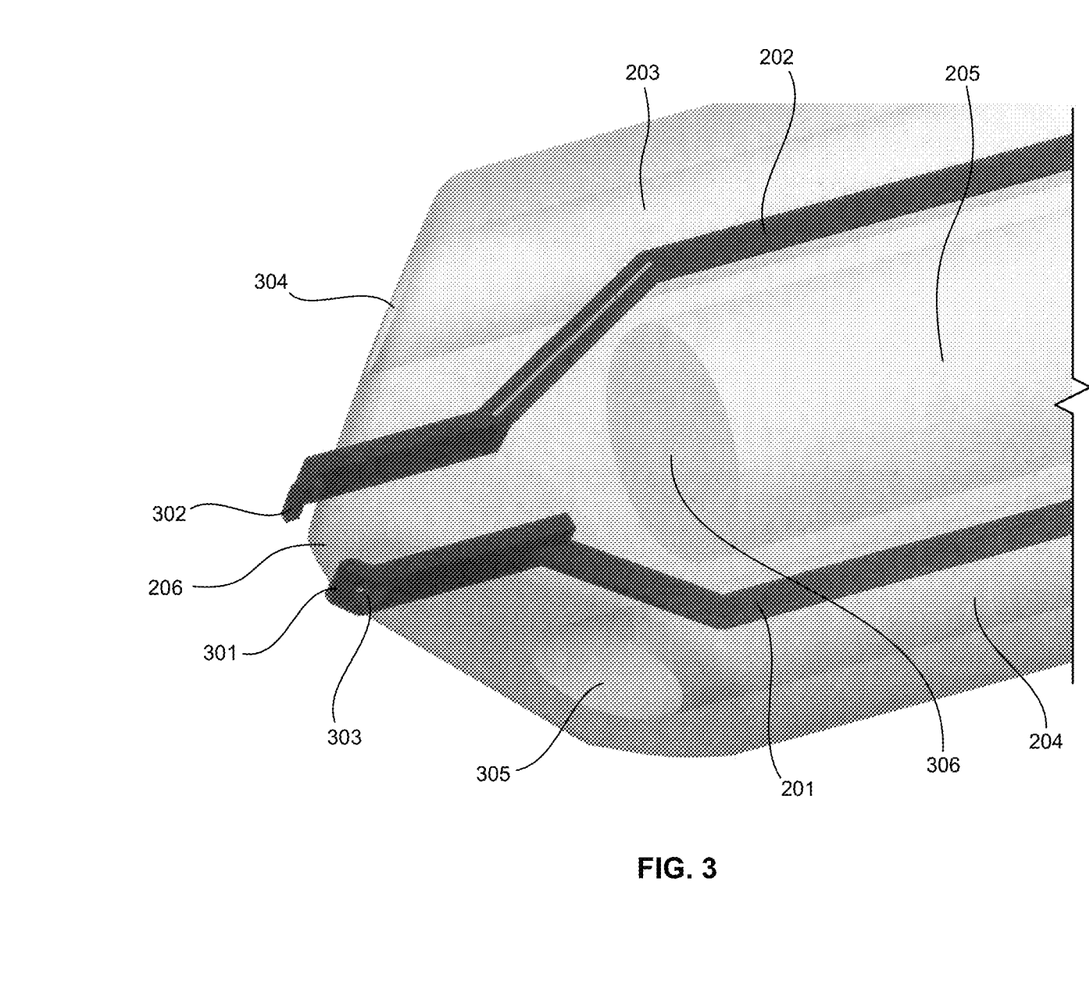
FIG. 3 is an enlarged view focusing on the tip of the ablator tool of FIG. 2.

As shown in FIG. 3, a first electrode tip 301 and a second electrode tip 302 extend from electrodes 201, 202, and emerge from the distal end 206 of the ablator tool 101. The electrode tips 301, 302 remain separated outside the ablator tool 101, thereby creating an open circuit. When both tips 301, 302 are placed in contact with tissue (e.g. spinal disc tissue) the circuit is closed, allowing RF energy to flow between the tips.

An alternative embodiment of ablator system may include an electrocautery pad as a return element. One way to minimize the chance of internal RF energy arcing is to have only one electrode embedded in a tool and locating a return element outside the tool, such as an electrocautery pad. U.S. Pat. No. 7,771,419, the disclosure of which is hereby incorporated by reference herein, describes a pad that can be used with the ablator system. The pad disclosed adheres to the outside of a patient's body during electrosurgery so that energy from a single electrode can flow into intended tissue, through a patient's body, and into the electrocautery pad where it returns to a control unit.

Figure 1:
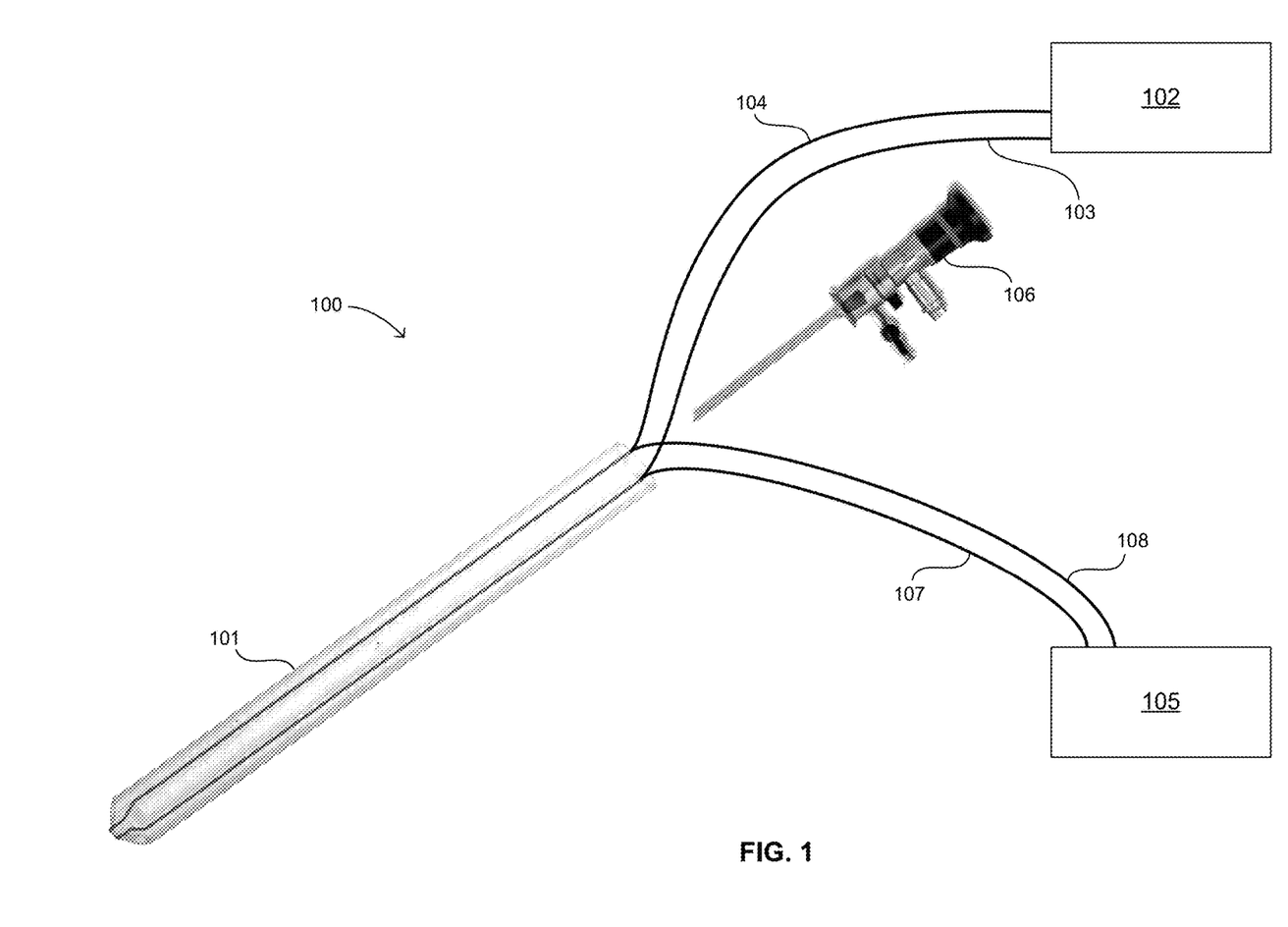
FIG. 1 is an illustrative embodiment of a spinal disc ablator system of the present invention.

Wires 103, 104 connect the proximal ends of the electrodes 201, 202 to a control unit 102 (best shown in FIG. 1). Control unit 102 generates the RF energy necessary for ablation and measures the impedance between electrode tips 301, 302. A control unit 102 can also temporarily stop producing energy if the measured impedance is not within an acceptable range. U.S. Pat. No. 5,540,684 ("the '684 patent") which has a common inventor with the current application and is hereby incorporated by reference herein, describes one suitable control unit for use with the current invention, although other control units are contemplated. The '684 patent describes a device and method for supplying RF energy to an electrosurgical tool, measuring impedance during the RF surgical procedure, and implementing safety measures (such as temporarily ceasing power) when the impedance is not within an acceptable range. Although the '684 discusses a method of RF control, the technology was directed to a pair of forceps which cannot be utilized in a spinal disc.

In other embodiments, the determination to continue supplying RF energy can be based on a safety factor. For example, bone has an electrical impedance value higher than that of tissue by a factor of four or more. A control unit may cease to provide energy if impedance changes by a factor of, say, three or more. This can be particularly effective in situations where tissue has a broad range of impedance values but is relatively low compared to bone. The control unit could also cease providing energy if the impedance drops outside an acceptable range.

In operation, control unit 102 supplies RF energy to first electrode 201 through a first wire 103. The energy travels through the first electrode 201 into a first electrode tip 301, through the spinal disc tissue, and into a second electrode tip 302. Ablation occurs when energy passes through tissue at a high enough level. The energy then travels from second electrode tip 302, through a second electrode 202, and along a second wire 104 to return to control unit 102. Control unit 102 can determine the impedance between electrode tips 301, 302 based on the voltage and current differences between the energy sent to the first electrode and that returned by the second electrode.

In some embodiments, the control unit can have a safety feature where if the energy sent out of the first electrode does not equal the energy returned by the second electrode, the control unit will cease to provide power. When the energy out is greater than the energy returned the energy differential is being expended somewhere in the patient's body and can cause damage by burning unintended tissue.

The control unit is preferably wired to an activation switch. The switch is used to activate the flow of RF energy to a first electrode. However, it may be preferable to allow a surgeon or medical professional to control the RF energy (as well as the pump system) through a remote device. Therefore, one alternative embodiment of the ablator system has a foot pedal to activate the control unit. U.S. Pat. No. 7,883,458, which is hereby incorporated herein, discloses a wireless foot pedal for controlling medical devices. The foot pedal communicates with a receiver which can be electrically connected to a control unit, in place of an existing wired controller. As described, the foot pedal can have multiple switches to allow individual activation and adjustment of the control unit as well as irrigation and suction, from a pump system. The remaining aspects of ablation system can continue to function as described herein when the wireless foot pedal is used.

Although vaporization is the goal of ablation, the tissue can be burned if it is not fully heated to the vaporizing temperature. It is detrimental to a patient's health to leave burned tissue in the body as it may be carcinogenic. It is therefore beneficial for a surgeon or medical professional to observe the surgical site during the ablation process to ensure that no burned tissue remains in the patient's body from the procedure.

Figure 4:
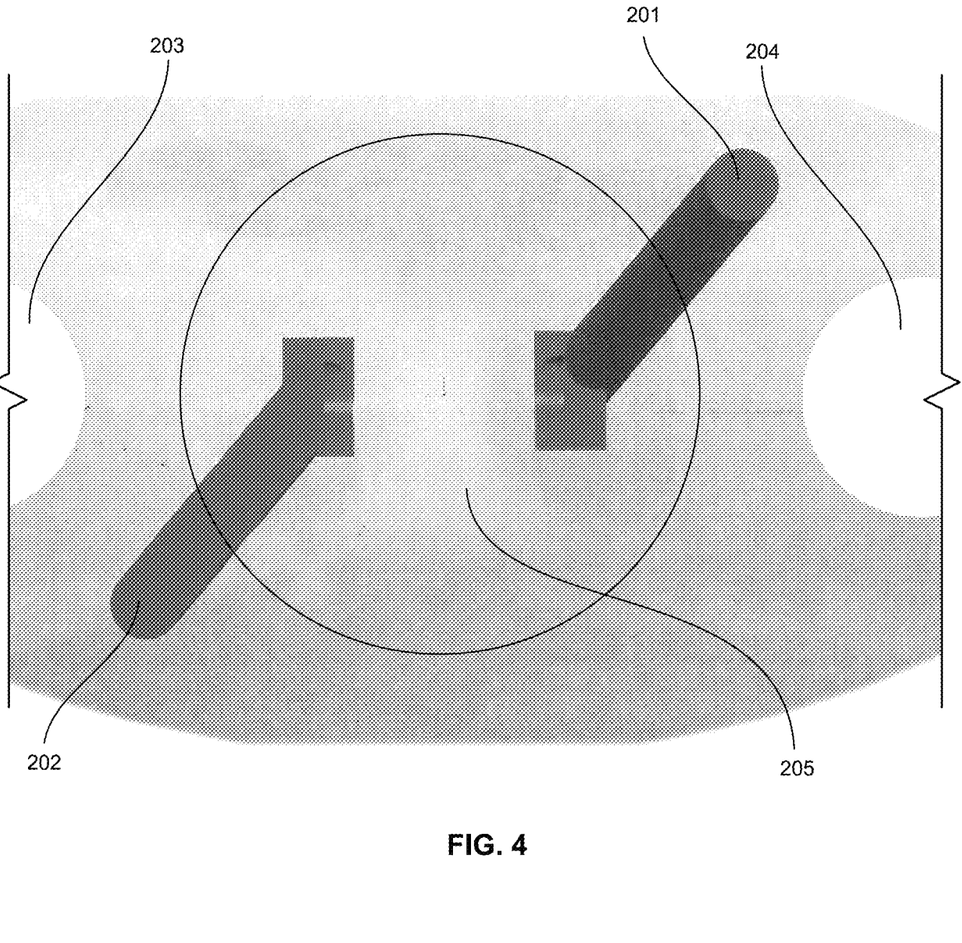
FIG. 4 is a view showing the interior of the ablator tool of FIG. 1 looking from the proximal end toward the distal end from the perspective of the scope.

A scope 106 (for example, an Olympus 1.9 mm MiniTrueView Arthroscope) can be inserted into ablator tool 101 to provide visualization of the surgical site during operation of the ablation system 100. A scope, as the term is used herein, could refer to a gastroscope, choledoscope, endoscope, or other similar scope used in surgical procedures that provides visual feedback. A channel 205 extends from the proximal end 207 toward, but terminating prior to, the distal end 206 of ablator tool 101 (best shown in FIGS. 2-4). FIG. 4 shows a view inside the channel 205 looking toward the distal end 206. As shown, the distal end 206 of the ablator tool 101 is composed of an optically clear material such as a thermoplastic (for example, polycarbonate, acrylic) so the scope can capture images outside the ablator tool. While the remaining portions of the ablator tool could also be transparent, only the distal end through which the scope captures images is required to be transparent.

In alternative embodiments where a flexible ablator tool is adopted, the diameter of a tool and channel could be adjusted to accommodate a flexible scope (for example, an Olympus CHF type BP30 which has a distal end diameter of 3.1 mm). A self-articulating scope could also function as an actuating mechanism to manipulate a flexible ablator tool.

Alternatively, the articulation driver to maneuver the tool could be incorporated into ablator tool itself using techniques similar to that disclosed in U.S. Pat. No. 5,595,565. However, other methods of control are also contemplated. A passive coherent optical fiber bundle can be used in place of a scope to provide visualization when the articulation driver is part of ablator tool itself.

Ablation can sometimes create debris at the surgical site. Debris that remains free to move around in a spinal disc during a procedure can interfere with the visualization provided by the scope. The debris may even adhere to the end of the ablation tool, further limiting visibility. It is therefore desirable for an ablation tool to extract debris from the site while at the same time providing a way to dislodge any tissue adhering to the end of the tool.

The ablator system also provides irrigation and suction at an internal surgical site. Ablator tool 101 has an irrigation port 203 and a vacuum port 204 (best shown in FIGS. 2-4) to remove any debris at a surgical site. Ports 203, 204 extend from the proximal end 207 to the distal end 206 of ablator tool 101. The distal ends of ports 304, 305 are farther from the axis of the ablator tool 101 than the electrode tips 301, 302. Positioning the ports 304, 305 outside the tips 301, 302 increases the likelihood of the irrigation flowing over the tips 301, 302 to clear them of any debris. The electrode tips 301, 302 each have at least one hole 303 for the irrigation to flow through to further facilitate the irrigation clearing the tips and tool of any debris. Irrigation can also increase electrical conductivity between electrode tips and tissue when a fluid such as saline is used.

As shown in FIG. 1, the proximal ends of ports 203, 204 are coupled to a pump system 105 (e.g. a Stryker FloControl Arthroscopy Pump) by tubes 107, 108. The pump system 105 preferably provides irrigation and suction at variable pressures and can be activated and deactivated, independently of each other, on demand by the operator. The pump system referenced has a controller wired to it. However, the wireless foot pedal described above could also be used to control the pump system.

In use, irrigation fluid (for example, saline) is supplied to an ablator tool 101 through an irrigation tube 107. Fluid flows from an irrigation tube 107, through an irrigation port 203, and out an irrigation port outlet 304. The irrigation then flows around electrodes 301, 302, through flow-through holes 303, and across the distal end 206 of ablator tool 101 to wash away debris. Suction provided by pump system 105 enables ablator tool 101 to remove the irrigation along with any debris immersed in the fluid. Pump system 105 creates suction which causes irrigation to enter a vacuum port inlet 305 and flow through a vacuum port 204, through a suction tube 108, and return to pump system 105.

In other embodiments, an ablator tool may have only one port that is configured for either irrigation or suction. In some instances the use of both irrigation and suction may not be necessary. For example, shorter surgeries may not require the use of suction or a surgeon may choose to forego irrigation as a cost saving measure. A single port tool can also have a smaller cross-sectional area, making it easier to maneuver the ablator tool into small spaces.

Figure 5:
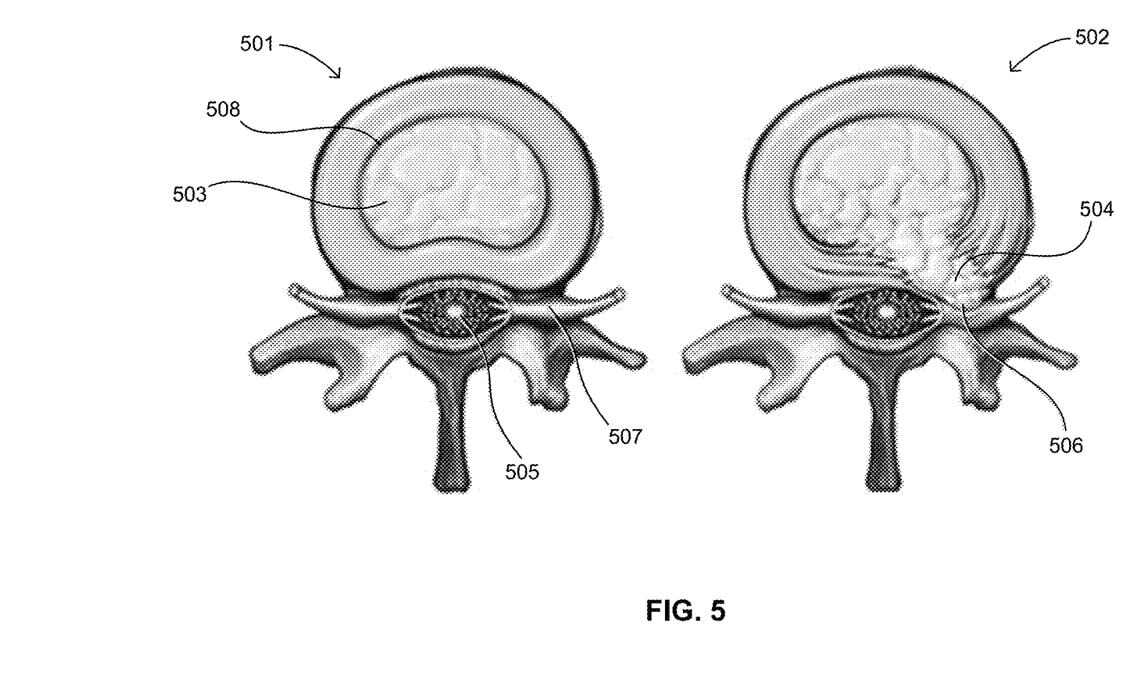
FIG. 5 is a comparison of a normal spinal disc and a herniated spinal disc with a compressed nerve root.

FIG. 5 shows a normal spinal disc 501 compared to a herniated disc 502. A normal disc 501 has a continuous perimeter 508 that confines spinal disc tissue 503. A nerve root 507 adjacent to a normal disc 501 remains free from interference. In contrast, a herniated disc 502 has a breached perimeter 508 that allows bulging tissue 504 to exert pressure on a compressed nerve root 506. A compressed nerve root can cause a person to suffer anything from slight discomfort to severe pain. A spinal disc ablator system 100 can relieve that pressure by ablating the bulging tissue 504.

Figure 7:
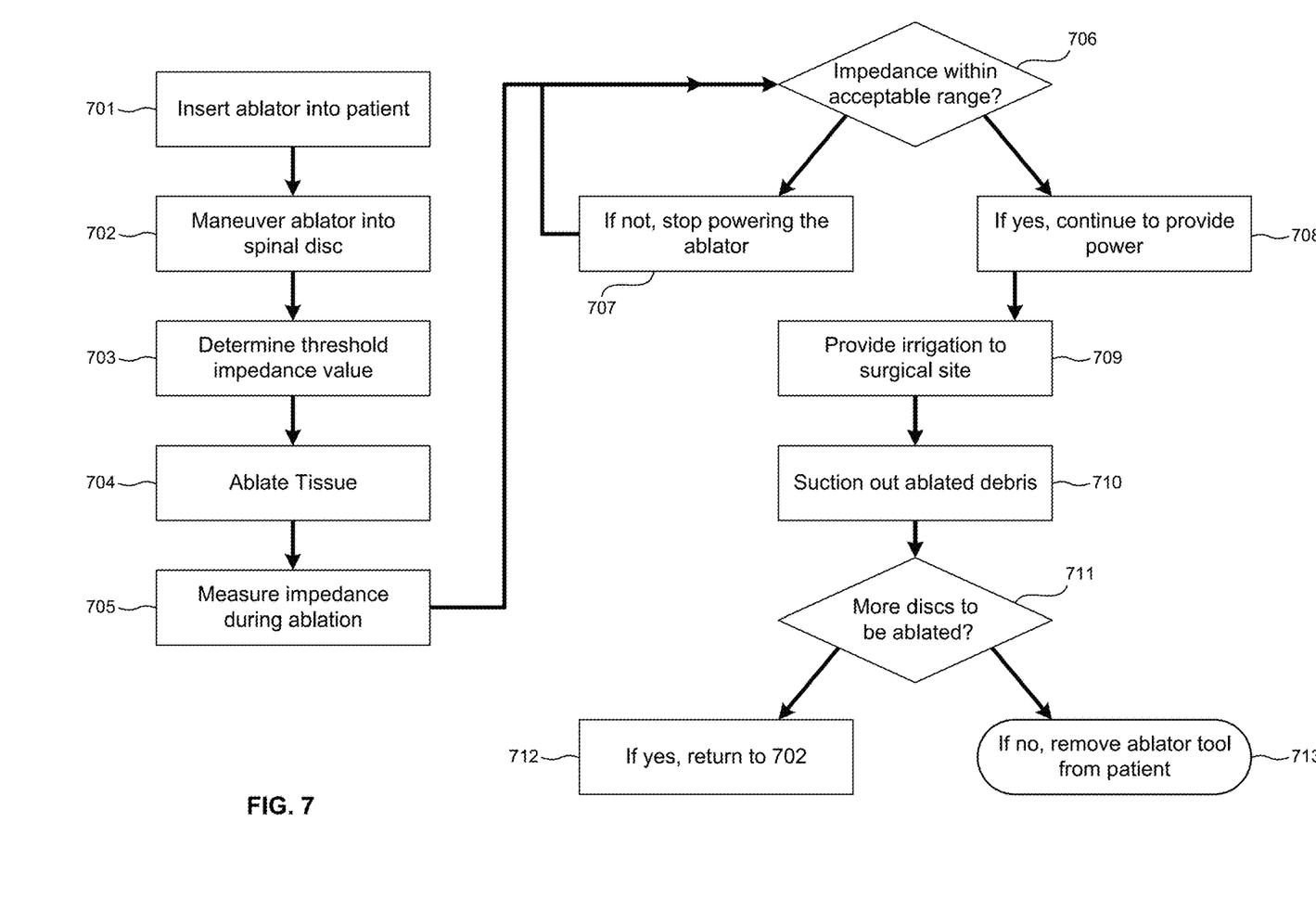
FIG. 7 is a flowchart showing the process of ablating a spinal disc in accordance with one embodiment of the current invention.

FIG. 7 shows a method of using a spinal disc ablator system in accordance with one embodiment of the invention. An ablation procedure begins when a surgeon inserts an ablator tool 101 into a patient (task 701). A surgeon makes an initial incision with a surgical instrument and inserts an ablator tool through that incision.

Figure 6:
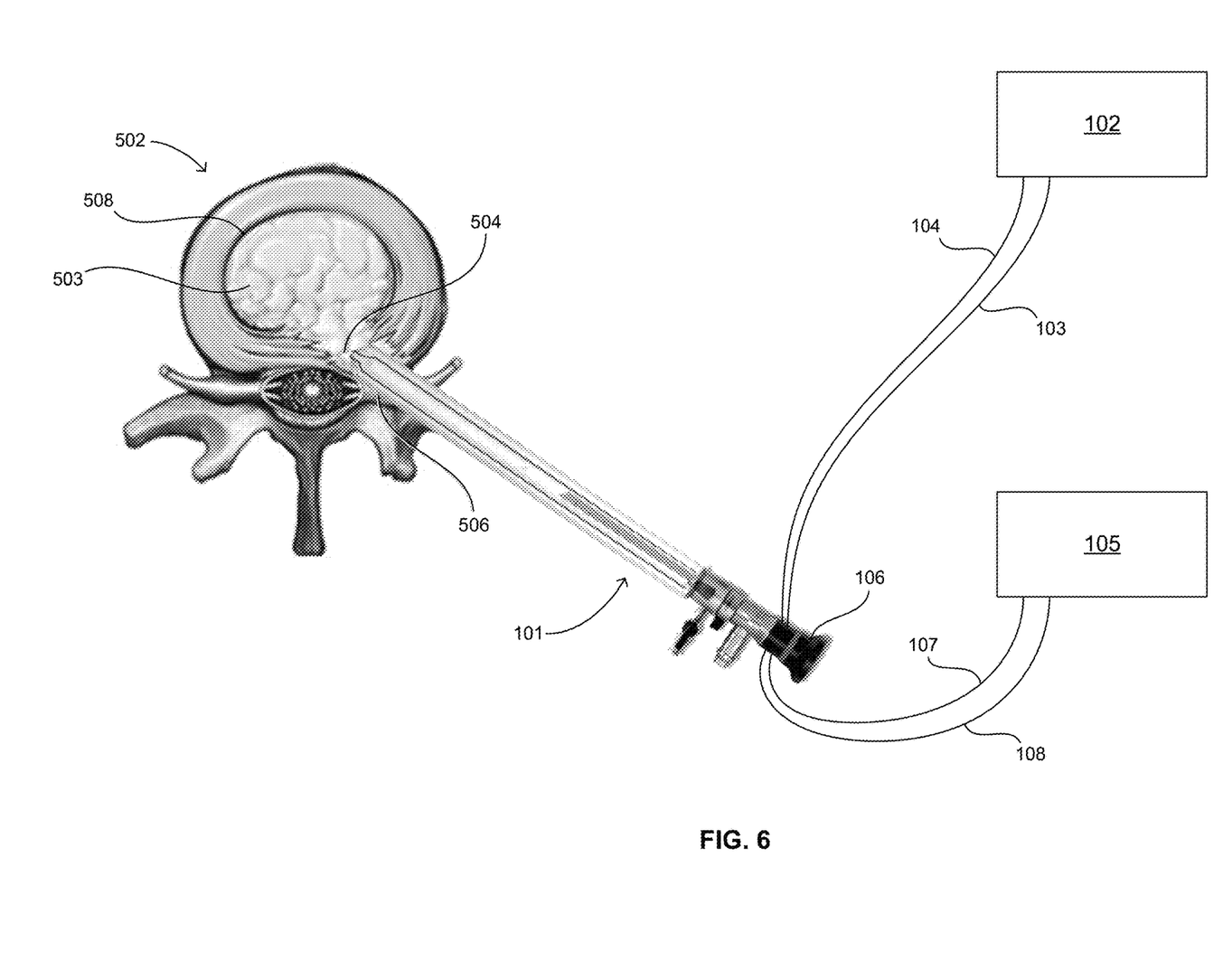
FIG. 6 depicts the ablator tool inserted into a spinal disc during an ablation procedure involving the spinal disc ablator system.

A surgeon maneuvers an ablator tool 101 into a spinal disc based on visual feedback provided by a scope 106 coupled to ablator tool 101 (task 702). Maneuvering continues until a distal end of an ablator tool 101 is inserted into a herniated disc 502 as shown in FIG. 6.

A threshold impedance value is determined before ablation occurs. Control unit 102 measures the initial impedance of spinal tissue 503 when an electrical circuit formed by an electrode tip 301, tissue, and a return element in the form of a second electrode tip 302 is closed (task 703). A threshold impedance value is determined based on the measured initial impedance.

In other embodiments, a threshold value may be determined from previously known values. For example, an average impedance value for spinal vertebrae or spinal discs could be stored in a control unit prior to a procedure and those values could be used in place of a measured value.

In still other embodiments, the threshold value can be determined by touching the various tissues at the surgical site and measuring their respective impedance values. For example, when the ablator tool is used in a spinal procedure, the surgeon could touch the tissue intended to be ablated with ablator tool and record the impedance. The ablator tool could then be placed in contact with the spinal nerve and bone and record their respective impedance values. An acceptable range can be determined based on those values. These patient specific impedance values can improve the performance of the system by providing a more accurate determination of what material the tool is in contact with, thereby allowing more complete ablation of the intended tissue.

Tissue is ablated after a threshold impedance value is determined (task 704). Control unit 102 generates RF energy and transmits it along a first wire 103. The energy transfers from the wire 103 through a first electrode 201, to a first electrode tip 301. The energy then flows through spinal tissue and into a second electrode tip 302 where it travels through a second electrode 202 a second wire 104 then returns to control unit 102. Tissue is ablated when the RF energy passes through it and the inherent electrical resistance of tissue causes the temperature to rise to its vaporization point. In other embodiments where an ablator tool has only one electrode, energy can pass from the electrode through the tissue and other parts of the body before entering an electrocautery pad to return to a control unit.

Impedance between an electrode and a return element is measured during ablation (task 705). The measured impedance value is compared to a threshold impedance value (task 706). If the measured impedance is outside of an acceptable threshold value range the RF energy is temporarily discontinued (task 707). The system then returns to task 706 to determine whether the impedance is with an acceptable threshold value range. In this manner, the system is continuously measuring the impedance while the tool is in use. If the measured impedance is lower than a threshold value a control unit 102 will continue to generate RF energy (task 708).

A surgeon or medical professional activates a pump system 105 to provide irrigation at the surgical site (task 709). Irrigation washes away any debris created during the ablation process from the surgical site, electrical tips, and ablator tool. In other embodiments, a surgeon may supply irrigation to a surgical site before or concurrently with ablation.

Suction from a pump system is activated to remove debris and irrigation from the site (task 710). Visual feedback is improved when excess material is removed from the spinal disc. A surgeon will be able to more accurately determine whether additional tissue needs to be ablated when there is a clear view of the disc.

A surgeon is able to ablate more than one disc during a procedure using the ablator system. After ablating tissue in a first disc a surgeon must determine if additional discs should be ablated (task 711). If more discs should be ablated the process can continue from task 702. If all discs have been ablated the surgeon can remove ablator tool 101 from the patient, completing an ablation procedure (task 713).

The ablator tool of the present invention can also be used in other spinal surgical procedures where access to the disc space is required. For instance, spinal fusion procedures often require the complete or partial removal of the disc in order to allow for the implantation of an interbody device between the vertebrae of the spine (for example, the Stryker Adaptive Vertebral PEEK Spacer (AVS) AL). Thus, the ablator tool can be utilized in order to provide anterior, posterior, or lateral access to the disc space. When used in such a procedure, the ablator tool is placed at the surgical site as described above. However, instead of only ablating the tissue from a herniated disc, at least a portion of the disc itself is vaporized. The ablator tool is removed, thereby granting access to a disc space formerly occupied by the spinal disc. The interbody device can then be inserted into the disc space to replace the disc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An RF surgical system for spinal disc ablation comprising:
    an ablator tool having a proximal end and a distal end;
    at least one port formed from said proximal end to said distal end of said ablator tool;
    a first electrode to expel energy embedded within said ablator tool with a first electrode tip extending beyond said distal end of said ablator tool;
    a second electrode to receive electrical energy expelled by said first electrode, said second electrode embedded within said ablator tool and including a second electrode tip extending beyond said distal end of said ablator tool;
    at least one channel formed within said ablator tool extending from said proximal end toward said distal end; and
    a scope within said at least one channel adapted to provide visualization between said first electrode and said second electrode,
    wherein said first electrode tip and said second electrode tip each include a hole therethrough.

2. The RF surgical system of claim 1, wherein said ablator tool comprises a modified multiple port endoscope having at least one electrode.

3. The RF surgical system of claim 1, further comprising a control unit electrically connected to said first electrode and said second electrode to generate and transmit RF energy to said first electrode.

4. The RF surgical system of claim 3, further comprising a remote device for activating said control unit.

5. The RF surgical system of claim 3, wherein said control unit measures an impedance between said first electrode and said second electrode and ceases to provide RF energy to said first electrode if said measured impedance is outside of an acceptable threshold impedance value range.

6. The RF surgical system of claim 1, further comprising at least one of an irrigation pump and a vacuum pump fluidly connected to said at least one port.

7. The RF surgical system of claim 1, further comprising at least two ports;
an irrigation pump fluidly connected to one of said at least two ports; and
a vacuum fluidly connected to the other of said at least two ports.

8. The RF surgical system of claim 7, further comprising a pump system to provide irrigation and suction to said ablator tool.

9. The RF surgical system of claim 8, further comprising a remote device for activating said irrigation and said suction.

10. The RF surgical system of claim 1, wherein said ablator tool is flexible and is driven by at least one of an articulating scope and an articulation driver incorporated into said ablator tool.

11. The RF surgical system of claim 1, wherein the at least one port further comprises a first port and a second port, the first port and the second port positioned so that both the first and the second electrodes are positioned therebetween.

12. The RF surgical system of claim 1, wherein the first electrode tip and the second electrode tip are fixed relative to the ablator tool and are each located at a first distance from the proximal end of the ablator tool.

13. A method of ablating tissue in a spinal disc comprising: maneuvering an ablator tool into a spinal disc based upon visual feedback provided by said ablator tool;
transferring energy from a first electrode tip of a first electrode extending beyond a distal end of said ablator tool, through spinal tissue, and into a second electrode tip of a second electrode extending beyond said distal end of said ablator tool, whereby said spinal tissue is ablated by said energy transfer;
providing irrigation fluid through said ablator tool, said irrigation fluid passing through a first hole in said first electrode tip and a second hole in said second electrode tip; and
suctioning at least one of said irrigation fluid and said spinal tissue through said ablator tool.

14. The method of claim 13, further comprising measuring an impedance between said first and second electrodes at least during said transferring energy step, comparing said measured impedance to a threshold value, and at least temporarily ceasing to provide energy to said first electrode if said measured impedance is outside of an acceptable threshold value range.

15. The method of claim 14, wherein said acceptable threshold value range is determined by placing at least the first electrode in contact with materials at said surgical site, recording their impedance values, and formulating a range based on those values.

16. The method of claim 13, further comprising maneuvering a self-articulating, flexible ablator tool.

17. The method of claim 13, wherein said spinal tissue to be ablated is bulging tissue from a herniated disc.

18. A method of spinal surgery comprising:
maneuvering an ablator tool into a spinal area based on visual feedback provided by said ablator tool;
vaporizing at least a portion of a spinal disc with a first tip of a first electrode extending from a distal end of said ablator tool contacting said spinal disc and a second tip of a second electrode extending from said distal end of said ablator tool contacting said spinal disc, said contact creating a closed circuit;
transporting debris from said spinal area via irrigation and suction provided by said ablator tool, said first tip and said second tip both having holes so that said irrigation passes therethrough;
rinsing an end of said ablator tool with said irrigation;
removing said ablator tool from a disc space formerly occupied by said spinal disc; and
inserting an interbody device into said disc space.

19. The method of claim 18, wherein access to a disc space is provided from at least one of anterior, posterior, or lateral directions.

20. The method of claim 18, wherein said portion of spinal disc removed is sized specific to said interbody device to be implanted.

* * * * *